United States Patent
King

(10) Patent No.: US 6,749,870 B2
(45) Date of Patent: *Jun. 15, 2004

(54) COMPOSITIONS AND METHODS FOR THE CONTROL OF SMOKING

(76) Inventor: Michael Glenn King, 21 Mur 97, Ballarut Victoria (AU)

(*) Notice: Subject to any disclaimer, the term of this patent is extended or adjusted under 35 U.S.C. 154(b) by 0 days.

This patent is subject to a terminal disclaimer.

(21) Appl. No.: 09/755,460

(22) Filed: Jan. 5, 2001

(65) Prior Publication Data

US 2002/0028775 A1 Mar. 7, 2002

Related U.S. Application Data

(60) Continuation of application No. 09/095,954, filed on Jun. 11, 1998, now Pat. No. 6,288,087, which is a division of application No. 08/809,400, filed as application No. PCT/AU95/00621 on Sep. 21, 1995, now Pat. No. 5,883,137.

(30) Foreign Application Priority Data

Sep. 23, 1994 (AU) .............................................. PM8353

(51) Int. Cl.$^7$ ........................... A61K 35/78; A61K 9/68; A61K 31/70; A61K 31/44; A01N 25/00
(52) U.S. Cl. ........................ 424/725; 424/440; 514/813; 514/340; 514/23
(58) Field of Search .............................. 424/195.1, 440, 424/725; 514/813, 340, 23

(56) References Cited

U.S. PATENT DOCUMENTS

| 4,305,942 A | | 12/1981 | Thiele et al. ................ 424/249 |
| 4,997,671 A | * | 3/1991 | Spanier ....................... 426/646 |
| 5,212,201 A | | 5/1993 | Wakashiro et al. ......... 514/532 |
| 5,612,357 A | * | 3/1997 | Keenan et al. .............. 514/343 |
| 5,656,255 A | * | 8/1997 | Jones et al. ................... 424/43 |
| 5,721,257 A | * | 2/1998 | Baker et al. ................. 514/343 |
| 5,883,137 A | * | 3/1999 | King ........................... 514/813 |
| 5,965,625 A | | 10/1999 | King ........................... 514/813 |

FOREIGN PATENT DOCUMENTS

| WO | WO9609042 | 3/1996 | .......... A61K/31/35 |

OTHER PUBLICATIONS

JP 4–46119, Takeda Chem Ind Ltd(1), application No. 2–154348, Feb. 17, 1992.*

* cited by examiner

*Primary Examiner*—Shengjun Wang
(74) *Attorney, Agent, or Firm*—Dann, Dorfman, Herrell & Skillman, P.C.

(57) ABSTRACT

A composition for the control of smoking which comprises: (a) a flavonoid in the form of an extract from *Eupatorium cannibium* or *Eupatorium Fortunei*, preferably euparin; (b) a cytochrome P450 inhibitor; (c) a sugar; (d) a source of phosphate; and, optionally, (e) one or more pharmaceutically acceptable carriers.

1 Claim, No Drawings

COMPOSITIONS AND METHODS FOR THE CONTROL OF SMOKING

CROSS REFERENCE TO RELATED APPLICATIONS

The present application is a continuation of U.S. patent application Ser. No. 09/095,954, filed Jun. 11, 1998, now U.S. Pat. No. 6,288,087, which is a division of U.S. application Ser. No. 08/809,400, filed Mar. 21, 1997 (now U.S. Pat. No. 5,883,137, issued Mar. 16, 1999), which is the U.S. national stage of PCT/AU95/00621, filed Sep. 21, 1995 and which claims priority of Australian Application No. PM 8353, filed Sep. 23, 1994. The entire disclosure of each of the aforementioned prior U.S. patent applications is hereby incorporated by reference herein.

This invention is directed to compositions for use in the control of smoking, and methods which control or reduce the desire to smoke.

Cigarette smoking is recognized world wide as a health risk. Compared to non-smokers, there is a clear increase in morbidity and mortality across all age groups of cigarette smokers. Apart from well described negative effects upon asthma (J. Wakefield, (1988) *Personality and Individual Differences*, 9(2):465–477), clinical contact with smokers provides anecdotal data supporting the notion that smoking is associated with breathlessness, fatigue, or reduced fitness. These deleterious health effects of cigarette smoking have been widely publicized. It is reported that many smokers are convinced that smoking is indeed a health hazard (S. M. Glynn and S. Sussman, (1990) *Hospital and Community Psychiatry* 41(9):1027–1028). Despite this conviction, approximately one adult in three continues to smoke (Australian Institute of Health and Welfare, (1992) *The Third Biennial report of the AIHW*, AGPS, Canberra).

Various proposals have been put forward for the control of smoking and for the treatment of withdrawal symptoms associated therewith. One proposal is the use of transdermal (or gum-delivered) nicotine as an anti-smoking therapy. This approach is based on the view that nicotine addiction is the primary chemical reason for smoking (see, for example, Australian Patent No 607214). Outcome studies have cast doubt upon the assumption that nicotine is the reason for smoking. Even when using a concomitant programme to treat the behavioural aspects of the smoking habit, the success of nicotine-based interventions are little better than placebo or psychological therapy alone (Buchkremer et al, (1991) *Pharmacopsychiatry* 24(3):96–102).

Hypnotism, acupuncture and other "natural therapies" have also been used for the control of smoking, again with little success.

There is accordingly a need for alternative treatments for the control of smoking.

In accordance with one aspect of this invention, there is provided a composition for the control of smoking, said composition comprising:

(a) a xanthine oxidase inhibitor;
(b) a cytochrome P450 inducing compound;
(c) a sugar;
(d) a source of phosphate; and, optionally,
(e) one or more pharmaceutically acceptable carriers or excipients.

In accordance with another aspect of this invention, there is provided a method for the control of the desire to smoke, which comprises administering to a subject in need of such treatment a composition which comprises:

(a) a xanthine oxidase inhibitor;
(b) a cytochrome P450 inducing compound;
(c) a sugar;
(d) a source of phosphate; and, optionally,
(e) one or more pharmaceutically acceptable carriers or excipients.

In another aspect this invention relates to the use of a composition comprising:

(a) a xanthine oxidase inhibitor;
(b) a cytochrome P450 inducing compound;
(c) a sugar;
(d) a source of phosphate; and optionally,
(e) one or more pharmaceutically acceptable carriers or excipients.

in the manufacture of a medicament for the control of smoking.

In a still further aspect of this invention there is provided agents for the control of smoking, which agent comprises:

(a) a xanthine oxidase inhibitor;
(b) a cytochrome P450 inducing compound;
(c) a sugar;
(d) a source of phosphate; and optionally,
(e) one or more pharmaceutically acceptable carriers or excipients.

The compositions according to this invention have surprisingly been found to control smoking. Reference to the control of smoking includes suppression of the desire or need to smoke. This may in turn result in a substantial reduction in the number of cigarettes smoked by an individual, or may result in a cessation of smoking. The applicants do not wish to place any limitations on the mechanism of action of the compositions of the invention. Clinical results, as described herein, demonstrate that the compositions of the invention suppress the desire or need to smoke.

As mentioned above, the compositions according to this invention comprise:

(a) a xanthine oxidase inhibitor;
(b) a cytochrome P450 inducing compound;
(c) a source of phosphate;
(d) a sugar; and, optionally,
(e) one or more pharmaceutically acceptable carriers or excipients.

The term "xanthine oxidase" as used herein will be understood to include xanthine dehydrogenase and xanthine oxidoreductase.

Xanthine oxidase inhibitors are well known in the art. The inhibitors block xanthine oxidase activity by a variety of mechanisms which include competitive inhibition (where the compounds act as antagonist), binding to xanthine oxidase at or near the active site thereby blocking enzymic activity, altering the conformation of the xanthine oxidase by binding to xanthine oxidase generally outside of the active site, binding or otherwise inactivating free radical agents produced by xanthine oxidase, or other mechanisms.

A first group of xanthine oxidase inhibitors are the flavonoids which may otherwise be referred to a bioflavonoids (see, for example, Harborne et al, (Eds), *The Flavonoids*, Academic Press, New York, 1975; Harborne et al, *The Flavonoids, Advances in Research Since* 1986, 1994; Princemail et al, (1987), 'Ginkgo Biloba extract inhibits oxygen species production generated by phorbol myristate acetate stimulated human leukocytes', *Experientia*, February 15

43(2), 181–184; Frage et al, (1987), 'Flavonoids as antioxidants evaluated in vitro and in situ liver chemiluminescence', *Biochem. Pharmacol.*, March 1 36(5): 717–720; Schmeda-Hirschmann et al (1987), 'Preliminary pharmacological studies on *Eugenia uniflora* leaves: xanthine oxidase activity', *J. Ethnopharmacol.*, November 21(2) 183–186; Zeng L. H. and Wu T. W., (1992), 'Purpurogallin is a more powerful protector of kidney cells than Trolux and allopurinol', *Biochemistry and Cell Biology*, 70:604–709; Siggins F. M., (1888), 'Analysis of the leaves of *Eupatorium purpurem*', *Am. J. of Pharm.*, 60:121–122; Manger C. C., (1894), 'Euparin', *Am. J. of Pharm.*, 66:120–124; Trimble H., (1890) '*Eupatorium purpurem*', *Am. J. of Pharm.*, February 62:73–80).

The flavonoids are a large group of secondary plant metabolites derived from flavan. The basic structure of the flavanoids is flavanone (flavan-4-one) from which the flavonoid derivatives flavonol (flavan-3-ol), flavone and flavonol are derived. The anthocyanins and catechols are derived from flavan and are to be regarded for the purposes of this invention as flavonoids (see *Concise Encyclopedia of Chemistry*, de Gruyter, 1994, particularly pages 77, 190 and 411 to 413). Examples of anthocyanins include cyanin, pelargonin, delphin, idaein, malvin, petunin, keracyanin, micocyanin, frasarin, paeonin, oenin, and chyrsanthemin, and the like. These compounds may be hydrolyzed by acids and glycosidases to the corresponding aglycons (anthocyanins). Sugar residues may be bound 3- or 5- positions of the anthocyanins. Catechol tannins are a group of tannins in which the monomeric units are flavan-3-ol (catechols) or flavan-3,4diol. Catechol is a 5,7,3',4'-tetrahydroxyflavan-3-ol. The above compounds are to be regarded as flavonoids for the purposes of this invention.

The most widely occurring flavanoids are the flavones. Flavones are yellow pigments of the flavonoid group which comprise the flavone, isoflavone or flavanone skeleton. Flavones occur widely in nature, for example, in blossoms, woods and roots, usually as glycosides or esters of tannic acid and can be readily extracted from these natural sources, using long established techniques well known in the art such as those described in *The Flavonoids, Advances in Research Since* 1986, Harborne et al, 1994. Examples of flavones include apigenin, chrysin, eupatorin, fisetin, genistein, hesperitin, kaempherol, luteolin, morin, myricetin and quercetin. Flavonoid compounds and other xanthine oxidase inhibitor within the scope of his invention may be extracted from a wide variety of plant species including *Eupatorium purpurem* (otherwise known as Gravel Root, Queen of the Meadow, or Jo Pye Weed), *Eupatorium cannibium* (otherwise known as Agrimany), *Eupatorium Fortunei* (the relevant extract being known as Peil lan, or Peilan) Ginkgo Biloba. Preferred examples are the compounds euparin and eupatorin, or plant extracts containing these materials. Euparin containing extracts from *Eupatorium purpurem* are commercially available from a number of distributors, such as Blackmores 'Gravel Root Extract' (Blackmores Pty Ltd, Balgowlah, New South Wales, Australia).

Additional examples of flavonoid or bioflavonoids which may be used in this invention include citrus bioflavonoid, vitamin P, vitamin P complex, rutin, orange peel bioflavonoid, grapefruit peel bioflavonoid, lemon bioflavonoid, lime bioflavonoid, narigenin, naringin, naringenis, delphinidin, phloretin, cyanic, catechin, morin, phloridzin, phloretin, 3-hydroxyflavone, 3-deoxyflavonol, isorhamnetin, tricin, chrysoeriol, eriodictyon, techtrochrysin, silybin, taxifolin, pinocembrim, galangin, robinin, diosmetin, kaempferide, rhamnetin and 30-methyl catechin.

Flavonoid compounds may be provided as plant extracts (for example, water and/or alcohol extracts) of plants such as *Eupatorium purpurem*, or as purified, or semipurified compounds. Synthetically manufactured analogues of flavonoid compounds are within the scope of this invention.

Other xanthine oxidase inhibitors which may be used in the invention include plant extracts with known or demonstrable xanthine oxidase inhibitory activity such as modified tannins, extracts from common tea, and extracts from oak bark or acorns. Examples of other xanthine oxidase inhibitors include: purine analogues (such as caffeine, theobromine, theophylline, etofylline and the like); quinazolines (including methaqualone hydrochloride); triazines (such as 1,2,3-triazine, 1,3,5-triazine, cyanuric acid, cyanuric chloride and the like); pyrazalo (3,4-d)pyrimidines, such as, for example, allopurinol and oxypurinol; and benzocycloheptenones, such as, for example, purpurogallin.

Xanthine oxidase (XO) inhibitory activity can be readily assessed by standard biological assays, such as described in *Biochem. Biophys. Acta*. (1992) 1112(2):178–182, which is incorporated herein by reference.

Compounds which bind or otherwise inactive free radicals produced by xanthine oxidase are to be regarded as inhibitors of xanthine oxidase. Such compounds include butylated hydroxyanisole, butylated hydroxytoluene, propyl gallate, sodium benzoate, pterins (*FEBS Lett* (1992) 304(2–3) 163–166), flavonoid compounds, superoxide dismutases, iron removing compounds such as desferrioxamine, glutathione, bilirubin, ubiquinones, plasma antioxidants such as albumin, water soluble antioxidants such as ascorbic acid, lipid soluble antioxidants such as the tociperhols, heme removing antioxidants such as haptoglobulin, zinc, magnesium, chromium, copper and manganese aspartates, and the like.

Xanthine oxidase inhibitors may be provided as plant/plant component extracts produced according to standard techniques in the art which are, for example, described in the *British Herbal Pharmacopeia*, 1990 Volume 1, British Herbal Medicine Association, United Kingdom, and, *The Flavonoids, Advances in Research Since* 1986, Harborne et al, 1994.

Cytochrome P450 is an important component in the hepatic mixed function oxidase system which metabolizes many drugs and other chemicals. In humans, the relevant enzyme is $P_3$-450. Cytochrome P450IA$_2$ is the liver form of the enzyme, (Kalow W., and Tang B., (1992) *Lin. Pharmacol. Ther.*, 49:44-48). Inducers of cytochrome P450 are well known and include: polycyclic aromatic hydrocarbons; chlorinated agents such as 2,3,7,8-tetrachlorodibenzo-p-dioxin; charcoal broiled meats, such as beef; barbiturates ((such as phenobarbital, methylphenobarbital, cyclobarbital and the like); natal and synthetic flavonoids, such as tangeretin, nobiletin and 5,6-benzoflavone; indoles such as indole-3-carbinol and indole-3-acetonitrile which may, for example, be extracted from cruciferous vegetables or alfalfa; and smokey components or smokey essences which may, for example, be produced by bubbling smoke through water (see, Shahidi, N. T., (1968) *Ann. NY. Acad. Sci.*, 151-822–832; Okey A. B., (1990) *Pharmacol Ther* 45:241–298; Kalow W. and Tang B., (1992) *Clin. Pharmacol. Ther.*, 49:44–48; Anderson K. E., and Kappas A., (1992) *Annv. Rev. Nutr.*, 11:141–167, particularly pages 142, 152, 153 and 155; Chung et al, (1985) *Carcinogenesis* 6(40:539–543; Lajinsky et al, (1964) *Science* 145:353–55; Conney et al, (1976) *Clin. Pharmacol. Ther.* 20:633–642; Kappas et al, *Clin. Pharmacol. Ther.* 23:445–450; and Pantuck et al, (1976) *Science* 194:1055–1057).

A preferred cytochrome P450 inducing compound is a "smokey" component or smokey essence. Smokey components or essences are widely commercially available and are used, for example, in cooking, herbal remedies and the like. Smoke essences may be prepared for example, by bubbling smoke from burning wood, meats, fibres, tobacco leaves, paper or the like, through water, and thereafter collecting the water soluble smoke essence. An example of one commercially available smoke essence is Gemini Hickory Liquid Smoke (distributed by Food Services International, P O Box 2068, Paterson, N.J., 07509, United States of America).

The sugar component may be selected from fructose, sucrose, or any other sugars (whether monosaccharides, disaccharides or polysaccharides) which promote uric acid production in man (*Medical Approaches to Human Nutritional*, Bland J., Ed., 1983, pp 133–177). Examples of such sugars include glucose, galactose, xylose, arabinose, fucose, rhamnose, galactosamine, guluronate, iduronate, mannuronate, starch of other sugar polymers. Fructose is particularly preferred.

The source of phosphate includes any phosphate source (for example, in the form of an inorganic phosphate or other phosphorous containing compound). Examples include, phosphoric acid solutions suitable for administration to humans, phosphate salts such as calcium phosphate, sodium phosphate and magnesium phosphate, and the like.

Vitamin D is capable of increasing the uptake of phosphorus in the gut. Therefore, an effective amount of Vitamin D may also be administered as a component of the composition of the invention so as to facilitate phosphate uptake.

The compositions of the invention may comprise from about 1% to about 40% w/w, more specifically about 10% to about 25% w/w of a xanthine oxidase inhibitor, such as an extract of *Epatorium purpureum*; from about 0.1% to about 10% w/w, more specifically about 0.5% to about 3% w/w, still more specifically about 1% w/w cytochrome P450 inducing compound, such as smokey essence; from about 10% to about 50% w/w more specifically about 15% to about 40% w/w, still more specifically about 20% to about 35% w/w sugar; and from about 0.2% w/w to about 10% w/w, more specifically about 0.25% to about 5% w/w, still more specifically about 0.4% to about 1% w/w of a phosphate component. The composition may include Vitamin D in the amount of about 0.05% to about 5% w/w. The respective amounts of the above components may be otherwise expressed on a w/v or v/v basis.

For ease of reference, the respective components of the composition of the invention may be referred to as active ingredients.

The compositions according to this invention include those suitable for oral, topical (including buccal and sublingual), parenteral (including subcutaneous, intramuscular, intravenous, intraperitoneal and intradermal) vaginal or rectal administration or by implanting (for example, using slow release molecules). The compositions may conveniently be presented in unit dosage form and may be prepared by any methods well known in the art of pharmacology. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Depending on the rate of administration, the active ingredients may be required to be coated in a material to protect the active ingredients from the action of enzymes, acids and other natural conditions which may inactivate the ingredients.

For oral administration, the pharmaceutical composition may be in the form of tablets, lozenges, pills, troches, capsules, elixirs, powders, granules, aqueous solutions, suspensions, emulsions, syrups and tinctures. Slow-release or delayed-release, forms may also be prepared, for example, in the form of coated particles, multi-layer tablets or microgranules.

Solid forms for oral administration may contain pharmaceutically acceptable binders, sweeteners, disintegrating agents, diluents, flavourings, coating agents, preservatives, lubricants and/or time delay agents. Suitable binders include gum acacia, gelatin, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange, or raspberry flavouring. Suitable coating agents include polymers or copolymers of acrylic acid and/or methyacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium disulphate. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carries include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or cetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono or di-oleate, -stearate or -laurate and the like. The emulsions for oral administration may further comprise one or more emulsifying agents. Suitable emulsifying agents include dispersing agents as described above or natural gums such as gum acacia or gum tragacanth. For topical administration, the pharmaceutical composition may be in the form of a cream, ointment, gel, jelly, tincture, suspension or emulsion. The pharmaceutical composition may contain pharmaceutically acceptable binders, diluents, disintegrating agents, preservatives, lubricants, dispersing agents, suspending agents and/or emulsifying agents as described above.

The pharmaceutical forms suitable for parenteral administration include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (for example, glycerol, propylene glycol and liquid polyethylene glycol and the like), suitable mixtures thereof, and vegetable oils. Solutions or suspensions may further comprise one or more buffering agents. Suitable buffering agents include sodium acetate, sodium citrate, sodium borate or sodium tartrate. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, paraben, chlorobutanol, phenol, sorbic acid, thermerosal and the like. In many cases, it will be preferable to include isotonic agents, for example, sugars or sodium chloride. Prolonged absorption of the injectable compositions can be brought about, for example, by the use in the compositions of agents delaying absorption.

Sterile injectable solutions are prepared by incorporating the active ingredients in the required amounts amount in the appropriate solvent with various of the other ingredients enumerated above as required, followed by filtered sterilization.

Generally, dispersions are prepared by incorporating the various sterilized active ingredient or ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

For rectal administration, the active ingredient is suitably administered in the form of an enema or suppository. A suitable suppository may be prepared by mixing the active ingredient with a non-irritating excipient which is solid at ordinary temperatures but which will melt in the rectum. Suitable such materials are cocoa butter and polyethylene glycols.

Suitable enemas may comprise agents as described above with reference to forms for topical administration.

The above mentioned components used in formulating the active ingredients into suitable dosage forms may be collectively referred to as carriers and excipients. The compositions according to this invention are preferably suitable for oral administration, more preferably as aqueous solutions. An example of a solution according to this invention may comprise:
- (i) an aqueous/ethanol flavonoid containing extract, for example, extracted from the species *Eupatorium purpureum*;
- (ii) an aqueous solution of a smoke essence, such as hickory smoke essence;
- (iii) an aqueous solution of a phosphate compound such as phosphoric acid combined with fructose and glucose (commercially available from Rhone-Poulenc Rorer Australia Pty Limited under the trade mark Emetrol®- 10 ml of solution contains 3.75 g fructose, 3.75 g glucose, 50 mg phosphoric acid, lemon mint flavour, at a pH between 1.3 to 2).
- (iv) component (iii) may, for example, be replaced with separate aqueous solutions of:
- (v) glucose syrup or water;
- (vi) phosphoric acid; and
- (vii) flavouring.

According to the method of this invention the active ingredients may be administered separately, or alternatively as a composition containing each of the active ingredients (this representing an aspect of the present invention as set out above). In general, and without limiting the invention, a suitable dose of a xanthine oxidase inhibitor will be in the range of 0.5 mg to 10 mg per kg body weight, preferably in the range of 3 mg to 6 mg per kg body weight per day, and more preferably in the range of 4 mg to 5 mg per kg body weight per day. In general, and without limiting the invention, a suitable dosage range of a cytochrome P450 inducer will be in the order of 0.025 mg to 1 mg per kg body per day, preferably in the range of 0.15 mg to 0.6 mg per kg body weight per day, and more preferably in the range of 0.2 mg to 0.5 mg per kg body weight per day. In general, and without limiting the invention, a suitable dosage range of sugar will be in the order of 0.75 mg to 50 mg per kg body weight, preferably in the range of 4.5 mg to 30 mg per kg body weight per day, and more preferably in the range of 6 mg to 25 mg per kg body weight per day. In general, and without limiting the invention, a suitable dosage range of a source of phosphate will be in the order of 0.01 mg to 0.5 mg per kg body weight per day, preferably in the range of 0.06 mg to 0.3 mg per kg body weight per day, and more preferably in the range of 0.08 mg to 0.25 mg per kg body weight per day.

The precise amounts of the respective active ingredients utilized according to the composition and method of this invention may vary depending upon their activity, source, and like factors.

The respective components of the invention when in the form of a composition as described herein, may be administered from one to ten times per day, more preferably from three to five times per day, and administered at appropriate intervals and appropriate dosage levels. Administration may be maintained from one to ten weeks, preferably for at least two to four weeks.

The compositions of the invention may also have application in the treatment of fatigue, chronic tiredness, concentration difficulties, mood disturbance, or the general class of symptoms described as "asthenia" or "neurasthenia" or "post viral asthenia". Smokers may manifest one or more of these conditions which may result from various metabolic imbalances. A sign of such imbalance may be a strong urge to smoke. Treatment, or amelioration, of one or more of these conditions may result in a reduction of the urge or need to smoke.

The invention will now be described with reference to the following non-limiting examples.

EXAMPLE 1

A composition was prepared containing the following components:
- (a) 20% of volume of an extract of *Eupatorium purpureum*. This percentage is based upon the active component of a commercial source of the extract (Medi Herb, Gravel Root, *Eupatorium purpureum* Root, 1:2, Mediherb Pty Ltd, 124 McEvoy Street, Warwick Queensland 4370). A preferred adult intake of this component is 5 ml per day. The range of intake may be from 0.1 ml to 20 ml per day of that particular concentration of the extract, or more preferably 1 ml to 10 ml. Other forms of this extract, or extracts of other species of plant, or other manufactured antioxidants, may require different concentrations. In each case the preferred dose of this component is contemplated as being within the dose range generally accepted as the therapeutic range by relevant practitioners.
- (b) 1% by volume of a cytochrome P450 inducer in the form of hickory smoke extract (Gemini Hickory Liquid Smoke, Food Services International, Paterson, N.J., United States of America). A broad range of concentrations of "smokey essence" is possible, for example, from 0.1 % to 20% by volume.

(c) phosphorus plus sugar (fructose and glucose) embodied in the described form of this invention may be represented by the commercially available mixture Emetrol (Emetrol Solution, Lemon Mint Flavour—each 10 ml contains fructose 3.75 g, glucose 3.75 g, phosphoric acid 50 mg at pH 1.3 to 2, Rhone-Poulenc Rorer Australia Pty Ltd, 10–23 Paramount Road, West Footscray, Victoria 3012). The contemplated dose of fructose may be as high as 50 g per day. The mixture Emetrol and also serves as the carrier to which is added he other ingredients. The final mixture contained in every 100 ml is 20 ml of Eupatorium extract (Gravel root), 1 ml of hickory smoke extract and 79 ml of Emetrol.

EXAMPLE 2

A second composition according to the invention contained the following components:

(a) 1 kg glucose syrup, "Love Starches" product 43B, Lover Starches, Braidwood Street, Enfield, New South Wales, 2136, Australia;
(b) 200 ml Gravel Root, Gravel Root 1:1, Blackmores Pty Ltd, New South Wales, Australia,
(c) 500 ml water,
(d) 20 ml Hickory Smoke Essence, source as described previously,
(e) 10 ml Phosphoric Acid, 81% w/w, David Craig & Co, 2 Railway Terrace, Rocklea, Queensland, 4106, Australia,
(f) Lemon Essence "Queen" Brand, Flavouring Essence, Queen Fine Foods, 206 South Pine Road, Enoggera, Queensland, 4051, Australia,
(g) 1 kg Granular Fructose.

The glucose syrup may be used as a concentrated or dilute solution. As it functions as a carrier it may be replaced with other carriers or excipient.

EXAMPLE 3

Cessation of Smoking

Patient A was a fifty year old woman who wished to stop smoking and had previously unsuccessful attempted to stop smoking by hypnosis, acupuncture and self-help. Previous attempts to stop smoking generally lasted for up to three days, after which she began to feel desperate for a cigarette. The patient's reasons for wanting to stop smoking included chest problems and angina. The patient normally smoked up to twenty cigarettes a day. Patient A also reported feeling lethargic all the time.

Patient A was provided with the composition of Example 1. Treatment with the composition began on a Friday, with 10 ml doses being orally administered three to five times per day. No cigarettes where smoked during Friday and Saturday. The patient tried two cigarettes on the Sunday and reported that they tasted awful, and did not, attempt to smoke that day. On the Monday the patient reported "feeling great". On the Wednesday the patient reported feeling more energetic, and continued to abstain from smoking.

Two weeks from the commencement of the treatment the patient ceased to use the composition. Using the composition of this invention, the urge to smoke was overcome. Cigarettes tasted awful to when the patient tried to smoke on the third day following the commencement of the treatment. The patient continues to do without cigarettes and reports feeling much better.

EXAMPLE 4

Extended Trial

Thirty three subjects from a country town enrolled and completed a trial of the composition of this invention, as detailed below:

Administration of Composition:

The subjects were interviewed and provided with one 200 ml bottle of the composition of Example 1 (Tonic). The bottle of Tonic was expected to last for one week, and the subjects were instructed to return for a second bottle. The dosage rate was 10 ml of the Tonic taken three to five times per day.

Results:

The pretreatment smoking behaviour of the subjects is set out in Table 1

TABLE 1

| Pretreatment daily smoking behaviour (those completing the trial) | | | | | |
|---|---|---|---|---|---|
| Average 5.12 | | | n = 33 | | |
| Values | 2 | 3 | 4 | 5 | 6 | 7 |
| frequency | 3 | 2 | 2 | 12 | 9 | 5 |
| Percent | 9 | 6 | 6 | 36 | 27 | 15 |

"Values" represents the number of cigarettes smoked, and are coded thus:
(1) 1–5
(2) 6–10
(3) 11–15
(4) 16–20
(5) 20–30
(6) 30–40
(7) more than 40

Smoking behaviours was coded into seven categories of frequency with the majority (63%) claiming to be in either class 5 (20 to 30 per day) or class 6 (30 to 40 per day).

The post treatment smoking behaviour is shown in Table 2.

TABLE 2

| Posttreatment smoking behaviour | | | |
|---|---|---|---|
| Average 0.97 | | 0–4 | |
| Values | 0 | 1 | 2 | 4 |
| Frequency | 13 | 12 | 6 | 22 |
| Percent | 39 | 36 | 18 | 6 |

"Values", again representing the numbers of cigarettes smoked, and are coded thus:
(1) 1–5
(2) 6–10
(3) 11–15
(4) 16–20
(5) 20–30
(6) 30–40
(7) more than 40
(0) no cigarettes This data shows that 93% of trial participants were smoking less than ten cigarettes per day, with 75% smoking between none and five cigarettes. Thirty nine percent of subjects ceased smoking, the remainder reduced the number of cigarettes smoked per day. Longer term administration (over eight weeks) further increased the number of subjects who ceased smoking.

This example illustrates that the urge to smoke can be significantly reduced by utilizing the compositions of the invention, and that cessation of smoking was achieved in a large number of cases. Following one or two weeks of administration of the composition of Example 1, the most common smoking rate was zero, with over 80% of people smoking less than ten cigarettes per day. This reduced smoking rate was matched by reports of a dramatic reduction of the urge to smoke.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of said steps or features.

It is noted that all references referred to herein are specifically incorporated by reference.

What is claimed is:

1. A composition for the control of smoking, said Composition comprising:
   a. a flavonoid in the form of an extract from *Eupatorium Cannibium* or *Eupatorium Fortunei;*
   b. a cytochrome p450 inducing compound selected from the group consisting of polycyclic aromatic hydrocarbons, charcoal broiled meats, indols, and smokey essences;
   c. a sugar;
   d. a source of phosphate; and optionally
   e. one or more pharmaceutically acceptable carriers.

* * * * *